(12) United States Patent
Maasarani

(10) Patent No.: US 10,773,014 B2
(45) Date of Patent: Sep. 15, 2020

(54) PACKAGE FOR SYRINGE

(71) Applicant: Becton, Dickinson and Company, Franklin Lakes, NJ (US)

(72) Inventor: Karim Maasarani, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 816 days.

(21) Appl. No.: 14/246,727

(22) Filed: Apr. 7, 2014

(65) Prior Publication Data

US 2014/0215976 A1 Aug. 7, 2014

Related U.S. Application Data

(62) Division of application No. 13/549,646, filed on Jul. 16, 2012, now Pat. No. 8,727,117.

(51) Int. Cl.
*A61M 5/00* (2006.01)
*B65D 75/32* (2006.01)
*B65D 77/20* (2006.01)

(52) U.S. Cl.
CPC .......... *A61M 5/002* (2013.01); *B65D 75/326* (2013.01); *B65D 77/2032* (2013.01)

(58) Field of Classification Search
CPC ..... A61J 1/035; B65D 77/2064; B65D 75/36; B65D 77/10–40; A61M 5/002
USPC .......... 53/492; 206/570, 571, 363–366, 438, 206/370, 439, 531
See application file for complete search history.

(56) References Cited

U.S. PATENT DOCUMENTS

| | | | | |
|---|---|---|---|---|
| 3,036,700 A | * | 5/1962 | Krug | A61M 5/3202 206/365 |
| 3,093,242 A | | 6/1963 | Huyck et al. | |
| 3,342,319 A | | 9/1967 | Faulseit | |
| 3,353,664 A | * | 11/1967 | Armentrout | A61M 5/002 206/365 |
| 3,651,615 A | * | 3/1972 | Bohner | B29C 65/08 156/73.3 |
| 3,783,997 A | * | 1/1974 | Brown | A61M 5/002 206/365 |
| 3,927,762 A | * | 12/1975 | Zdarsky | B65D 75/28 206/229 |
| 4,106,621 A | * | 8/1978 | Sorenson | A61M 5/002 206/365 |
| 4,113,090 A | * | 9/1978 | Carstens | B65D 85/24 206/210 |

(Continued)

FOREIGN PATENT DOCUMENTS

CN 203638402 U 6/2014
EP 2272431 A2 12/2011
(Continued)

OTHER PUBLICATIONS

Final Office Action in U.S. Appl. No. 13/529,646, dated Oct. 10, 2013, 14 pages.

(Continued)

*Primary Examiner* — Dariush Seif
(74) *Attorney, Agent, or Firm* — Servilla Whitney LLC

(57) ABSTRACT

Packages comprising a syringe and a blister package are described. The blister package incorporates elements that allow one-handed opening. Also described are methods of removing a syringe from a package using only one hand.

11 Claims, 5 Drawing Sheets

(56) References Cited

U.S. PATENT DOCUMENTS

| | | | | |
|---|---|---|---|---|
| 4,184,593 A * | 1/1980 | Dorr | A61M 5/002 | 206/365 |
| 4,428,747 A * | 1/1984 | Friese | A61F 15/003 | 604/12 |
| 4,468,223 A * | 8/1984 | Minagawa | A61M 5/3202 | 604/199 |
| 4,581,023 A * | 4/1986 | Kuntz | A61M 5/24 | 604/234 |
| 4,842,326 A | 6/1989 | DiVito | | |
| 5,038,974 A * | 8/1991 | DaCosta | B65D 83/0055 | 222/106 |
| 5,407,070 A * | 4/1995 | Bascos | A61M 5/002 | 206/364 |
| 5,445,614 A * | 8/1995 | Haber | A61M 5/19 | 604/191 |
| 5,529,224 A * | 6/1996 | Chan | B65D 75/58 | 222/107 |
| 5,690,222 A * | 11/1997 | Peters | B65D 75/32 | 206/339 |
| 6,012,580 A * | 1/2000 | Peters | B65D 75/58 | 206/438 |
| 6,050,400 A | 4/2000 | Taskis et al. | | |
| 6,080,456 A * | 6/2000 | Fonteyne | A61L 2/26 | 428/35.7 |
| 6,186,325 B1 * | 2/2001 | Schmidt | A61M 25/002 | 206/364 |
| 6,228,324 B1 * | 5/2001 | Hasegawa | A61L 2/208 | 206/364 |
| 6,299,607 B1 * | 10/2001 | Osborn | A61F 13/15252 | 604/385.02 |
| 6,357,589 B2 | 3/2002 | Schmidt et al. | | |
| 7,713,244 B1 * | 5/2010 | Cherif Cheikh | A61C 5/04 | 604/187 |
| 8,056,716 B2 * | 11/2011 | Fonteyne | B32B 7/05 | 206/365 |
| 8,381,907 B2 * | 2/2013 | Kondo | A61F 13/551 | 206/438 |
| 8,727,117 B2 * | 5/2014 | Maasarani | A61M 5/002 | 206/364 |
| 9,333,289 B1 * | 5/2016 | Hirschmann | A61M 5/002 | |
| 2002/0027088 A1 * | 3/2002 | Discko, Jr. | A61M 35/003 | 206/229 |
| 2004/0112769 A1 * | 6/2004 | Perry | B65D 77/245 | 206/219 |
| 2005/0154354 A1 * | 7/2005 | Kawasaki | A61M 5/1785 | 604/232 |
| 2006/0275336 A1 * | 12/2006 | Du Plessis | A61L 2/0011 | 424/423 |
| 2007/0164045 A1 * | 7/2007 | Wydler | B65D 75/5866 | 222/106 |
| 2007/0250068 A1 * | 10/2007 | Vincent-Aubry | A61F 2/1678 | 606/107 |
| 2008/0035495 A1 * | 2/2008 | Discko, Jr. | A61M 35/003 | 206/209 |
| 2008/0202961 A1 * | 8/2008 | Sharp | A61M 5/002 | 206/364 |
| 2009/0107866 A1 * | 4/2009 | Dunn-Rankin | B65D 77/28 | 206/363 |
| 2009/0157008 A1 * | 6/2009 | Vitral | A61B 90/39 | 604/187 |
| 2010/0158991 A1 * | 6/2010 | Okada | A61F 13/551 | 424/448 |
| 2013/0233736 A1 * | 9/2013 | Hess | A61F 2/0095 | 206/210 |
| 2014/0138382 A1 * | 5/2014 | Willemsen | B65D 75/326 | 220/266 |
| 2014/0322075 A1 * | 10/2014 | Ferlic | A61L 2/235 | 422/28 |

FOREIGN PATENT DOCUMENTS

| | | | |
|---|---|---|---|
| JP | 11334757 A | * | 12/1999 |
| JP | H11334757 A | | 12/1999 |
| WO | 2014/014728 A1 | | 1/2014 |

OTHER PUBLICATIONS

Non-Final Office Action in U.S. Appl. No. 13/549,646, dated Apr. 2, 2013, 13 pages.

PCT International Search Report for PCT/US2013/050009, dated Dec. 2, 2013, 5 pages.

PCT International Preliminary Report on Patentability in PCT/US2013/050009, dated Jan. 29, 2015, 8 pages.

* cited by examiner

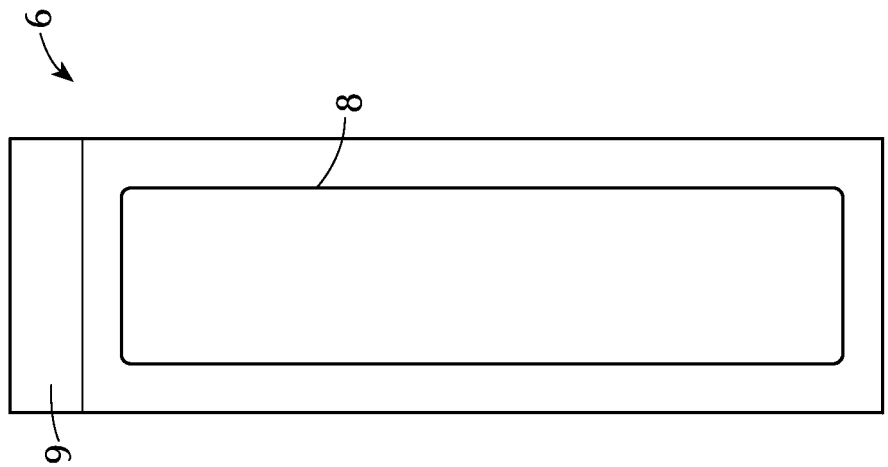
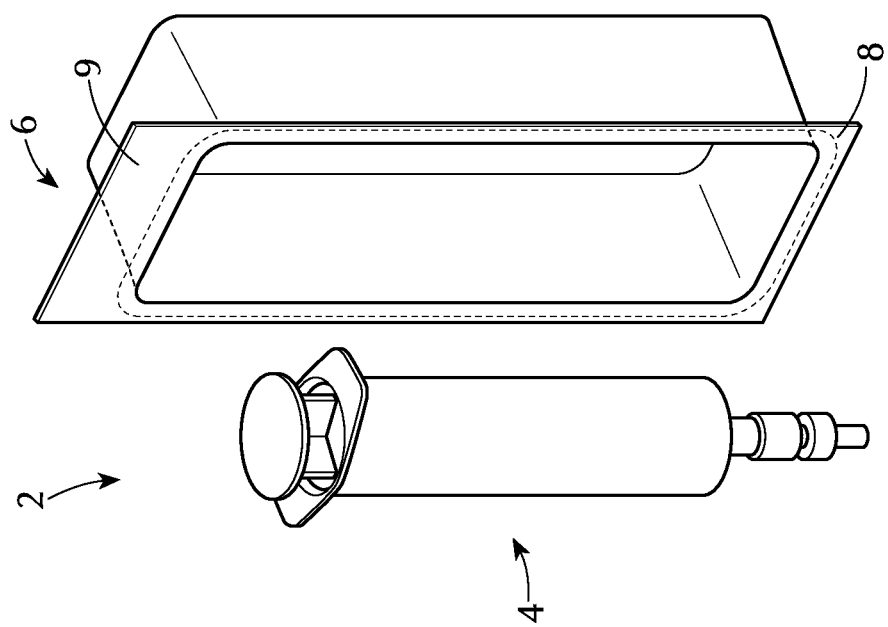

US 10,773,014 B2

PACKAGE FOR SYRINGE

CROSS-REFERENCE TO RELATED APPLICATIONS

This Application is a divisional of U.S. patent application Ser. No. 13/549,646 filed Jul. 16, 2012, the disclosure of which is hereby incorporated by reference in its entirety.

TECHNICAL FIELD

The present invention relates to packages, and more particularly to a package housing a syringe, wherein the syringe can be removed from the package using only one-hand.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the article, such as with a blister pack housing a syringe, so as to minimize the time period in which the article is exposed to unsterile conditions.

Traditionally, in order to prevent contamination, the syringe is loosely located within conventional blister packaging. The blister packaging provides an enclosure which is sealed against entrance of contaminants and prevents contamination of the syringe. Conventional blister packaging, however, requires two hands and the knuckle-roll-peel technique to open the packaging.

In the fast paced environment of a hospital or other medical setting, where there is little time to fumble with syringe packaging, this two-handed opening process is cumbersome and time-consuming. Medical technicians are often doing multiple tasks at one time, and, because of the design of conventional blister packaging, the technicians must free up both of their hands to open the blister package in order to make an aseptic presentation of the syringe.

Additionally, the traditional two-handed knuckle-roll-peel technique required to open conventional blister packaging often compromises sterility. The packaging, if opened in the wrong direction or in haste, can tear or fracture. This fiber tear is the delaminating of either the top or bottom web of the blister packaging material. Such tearing introduces foreign matter into the syringe product, exposing the syringe to unsterile conditions.

Furthermore, conventional blister packaging consumes a significant amount of material as the packaging requires a peel tab for the user to open the package. This extra packaging material leads to an increase in the cost of each syringe product. Moreover, the additional packaging then needs to be discarded upon opening the package, leading to an increase in the amount of waste material produced in a hospital or other medical setting.

FIGS. 1-4 show a conventional syringe package and opening of a conventional syringe package. FIGS. 1 and 2 illustrate a conventional syringe package. Referring to FIG. 1, the package 2 includes a syringe 4 and a blister package 6. The blister package 6 comprises a flexible web sealed to a backing thus defining a compartment and providing a sealed region 8 about the periphery of the backing for containing the syringe 4. The blister package also includes at least one peel tab 9 for the technician to use when opening the blister package to release the syringe. Referring to FIG. 2, the width of the sealed region 8 is equivalent around the entire periphery of the backing. In other words, whatever the sealing mechanism, the sealed region has the same dimension between the syringe and edge of the package around the entire package 6.

FIGS. 3 and 4 illustrate the opening of a conventional syringe package. Referring to FIGS. 3 and 4, with a knuckle-roll motion, the outer packaging material is peeled apart using two hands, and the product is released. In other words, the two-handed knuckle-roll-peel technique used to open the package 2 requires placing the knuckles of both hands on either side of the peel tabs 9 of package 2, and using the thumbs to roll and peel the seal apart, peeling the flexible web away from the backing to reveal the syringe 4 separate from the blister pack 6. This two-handed opening is very cumbersome and time-consuming for the technician, as it requires the technician to free-up both hands for opening the package. Additionally, the traditional two-handed knuckle-roll-peel technique required to open conventional blister packaging often compromises sterility. The packaging, if opened in the wrong direction or in haste, can tear or fracture. This fiber tear is the delaminating of either the top or bottom web of the blister packaging material. Such tearing introduces foreign matter into the syringe product, exposing the syringe to unsterile conditions.

It would be advantageous to provide a package to house a syringe that does not require the two-handed knuckle roll peel technique to open and that does not include a peel tab for opening.

SUMMARY

Aspects of the invention are directed to a package housing a syringe. Packages according to a first aspect of the present invention include a syringe and a blister package surrounding the syringe. The syringe typically will be sterile inside the package. The blister package comprises a flexible web sealed to a backing defining a compartment surrounding the syringe that enables the syringe to be squeezed out of the package. The features providing for removal of the syringe allow the syringe to be removed from the package with only one hand without comprising sterility.

In one or more embodiments, the syringe comprises a proximal region having a width and including a flange and a flange region, a distal region having a width, and a barrel extending from the proximal region to the distal region, the flange region having a width that is greater than the width at the distal region and the proximal region. The syringe is surrounded by a blister package. The blister package comprises a flexible web sealed to a backing defining a compartment surrounding the syringe and providing a sealed region about a periphery of the backing, the sealed region defining a proximal region seal width, a distal region seal width, and a flange region seal width, the flange region seal width substantially reduced adjacent the flange region compared to the distal region seal width to enable the syringe to be squeezed out of the package with one hand so that upon removal of the syringe from the blister package, the flange region and the proximal region exit the package prior to the distal region.

In one or more embodiments, the flange region seal width includes an escape point. The escape point permits the flange region to exit the package upon squeezing. The escape point can define an angled seal region having a seal width that is reduced compared to the distal region seal width. The angled seal region can comprise a point of a triangle, or the angled seal region can comprise at least two points forming a box.

In one or more embodiments, the flange region seal width can define a curved radius that enables the syringe to be squeezed out of the package with one hand.

In one or more embodiments, the flange region seal width is reduced adjacent the flange region compared to the distal region seal width. The flange region seal width can be reduced by at least ¹⁄₁₆, at least ⅛, at least ¼, or at least ½ adjacent the flange region compared to the distal region seal width.

A second aspect of the present invention is directed to a package comprising a syringe comprising a proximal region having a width including a flange and a flange region, a distal region having a width, and a barrel extending from the proximal region to the distal region, the flange region having a width that is greater than width at the distal region and the proximal region, the syringe surrounded by a blister package. The blister package comprising a flexible web sealed to a backing defining a compartment surrounding the syringe and providing a sealed region about a periphery of the backing, the sealed region having a shape that conforms to the shape of the flange so that the width of the seal adjacent to the flange is reduced compared to the width in the distal region.

In one or more embodiments, the width of the seal adjacent to the flange is reduced compared to the width in the distal region. The width of the seal adjacent to the flange can be reduced by at least ¹⁄₁₆, at least ⅛, at least ¼, or at least ½ compared to the width in the distal region.

A further aspect of the present invention is directed to a method of removing a syringe from a package. The method comprises squeezing the package of the invention with one hand so that upon removal of the syringe from the blister package, the flange region and the proximal region of the syringe exit the package prior to the distal region.

BRIEF DESCRIPTION OF THE DRAWINGS

FIG. 1 is a perspective view of a conventional syringe package and a syringe adjacent to the package;

FIG. 2 is a top plan view of a conventional syringe package;

DETAILED DESCRIPTION

Figure 3:
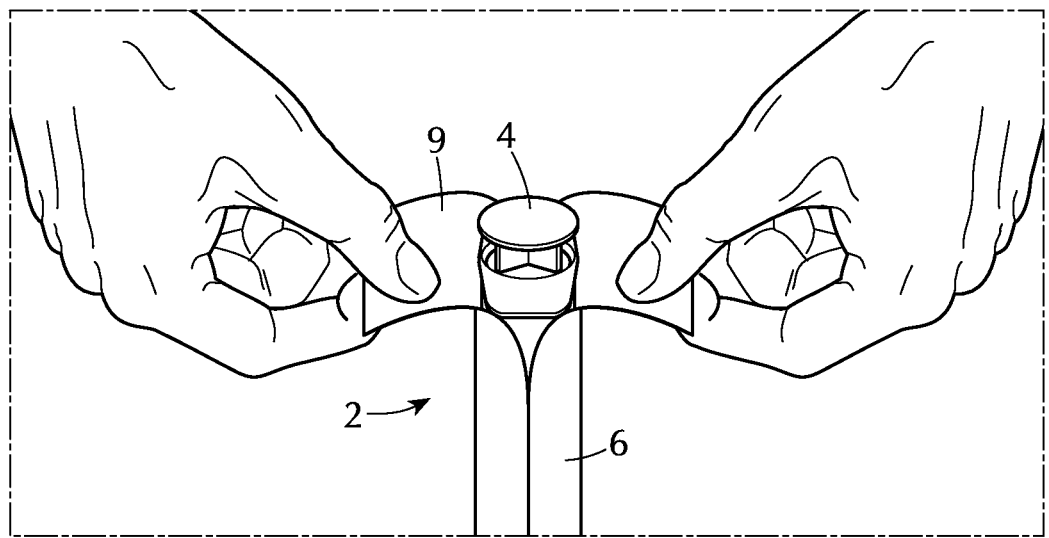
FIG. 3 is a perspective view showing a user/practitioner opening a conventional syringe package.
Figure 4:
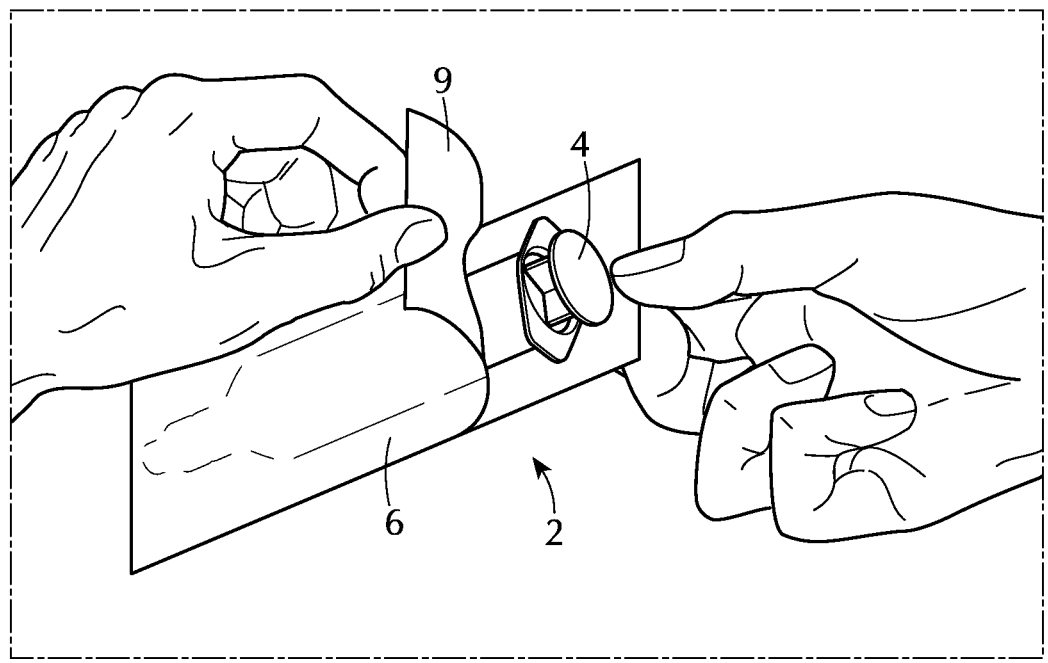
FIG. 4 is a side perspective view showing a user/practitioner opening a conventional syringe package.

Before describing several exemplary embodiments of the invention, it is to be understood that the invention is not limited to the details of construction or process steps set forth in the following description. The invention is capable of other embodiments and of being practiced or being carried out in various ways.

With respect to terms used in this disclosure, the following definitions are provided.

As used herein, the use of "a," "an," and "the" includes the singular and plural.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

As used herein, the terms "package" or "packaging" includes any material used to wrap or protect a good or product, such as a syringe. Packaging can be rigid or flexible. Packaging includes, but is not limited to, medical packaging, pharmaceutical packaging, and child-resistant packaging. Medical and pharmaceutical packaging can include blister packs.

As used herein, the terms "blister package" or "blister pack" includes several types of pre-formed packaging used for consumer goods, foods, pharmaceuticals, medical devices, etc. The primary component of a blister pack is a cavity or pocket made from a formable web, usually a thermoformed plastic. The formable web can be rigid or flexible. The cavity or pocket is large enough to contain the good which is housed in the blister package. Depending on the application, a blister pack may have a backing of thermoform able material and a lidding seal of aluminum foil, paper, Tyvek®, plastic, or other medical grade materials. Blister packs can also be hinged, clamshell containers, that can include a rigid backing, such as paperboard. Blister packages can provide barrier protection from microorganisms and other contaminants, and can provide a certain degree of tamper resistance. Within the many options that blister packaging provides, the blister pack must protect the product contained inside while still possessing the characteristic capable of making automated processing possible.

Blister packs are commonly used as unit-dose packaging for pharmaceutical tablets, capsules, or lozenges. The pharmaceutical product and its blister pack act together to serve as an integral unit. The blister pack protects the pharmaceutical product from outside influences that would otherwise render it useless while allowing the manufacturer of the pharmaceutical product to package it using form-fill-seal equipment. The form-fill-seal process involves creating the blister pack from rolls of flat sheet or film, filling with the pharmaceutical product, such as a drug tablet, and closing (sealing). This type of blister pack is sometimes referred to as push-through-packs because the consumer can push the good (e.g. drug tablet) through the backing. With pharmaceutical blister packs, manufacturers must be concerned with the moisture vapor transmission rate of the blister pack because many pharmaceutical products degrade and lose their efficacy through hydrolysis. Additionally, the blister pack must provide a barrier to oxygen in order to prevent degradation of the pharmaceutical product through oxidation. In one or more embodiments, the blister pack is a push-through-pack.

Blister packages that contain medical devices, such as a syringe, differ from pharmaceutical blister packs because medical blister packs are not push-through packages. Instead, the thermoformed base web is made of a thicker plastic and cannot be collapsed, thus forming a solid backing. The lidding film provides a peel-open feature that can be peeled open using two-hands, such as, e.g. the knuckle-roll-peel technique. The lidding film of a medical blister pack is generally porous to allow sterilization. Often, medical blister packs are made of Tyvek® or a similar medical grade material that is breathable and permeable to gases, but is not permeable to microorganisms. The lidding film can also be made of medical grade paper or a completely non-permeable or non-breathable film. In instances where a non-breathable film is used, sterilization is through radiation (e.g. electron beams (E-beam)). In one or more embodiments, the blister pack is a medical blister pack.

Blister packs can be created via thermoforming or cold forming. In the case of thermoforming, a plastic film or sheet is unwound from a reel and guided through a pre-heating station on the blister line. The temperature of the pre-heating plates is such that the plastic will soften and become pliable. The warm plastic then arrives in a forming station where a large pressure forms the blister cavity into a negative mold. The mold is cooled such that the plastic becomes firm again and maintains its shape when removed from the mold.

In the case of cold forming, an aluminum based-laminate film is simply pressed into a mold by means of a stamp. The aluminum elongates and maintains the formed shape. The use of aluminum offers a complete barrier for water and oxygen. However, cold form blister packs take longer to produce compared to thermoforming. Cold form blister packs are also not transparent, which can lead to consumers not complying with pharmaceutical therapies.

The thermoform able backing of the medical blister pack is generally comprised of a flexible thermoform able plastic film. The film is often multi-layered. The primary component is regularly a layer of approximately 15-30% Nylon, while the remaining layers can comprise substances including, but not limited to, polyethylene. The sealant layer can comprise, among others, ethyl vinyl acetate (EVA).

The lidding film of a medical blister pack can be made from plastic, aluminum, or medical grade papers that are permeable to gases for sterilization but are impermeable to microorganisms. Most commonly, Tyvek® is used as a lidding material for medical blister packs.

Blister packaging can also include the skin pack, where a paperboard or other backing material and product are covered with a thin sheet of transparent plastic. The backing generally has a heat-seal coating. The plastic film is softened by heat and draped over the product on the backing. Vacuum is sometimes used to assist in a snug fit. Immediately after forming the blister, the blister is transported to a vacuum sealing station where a vacuum is pulled and the blister is sealed shut, providing the snug fit. The plastic film bonds to the heat-seal coating on the paperboard or other backing. In one or more embodiments, the blister pack is a vacuum sealed thermoformed blister pack.

Blister packs can be sealed in a variety of ways including, but not limited to, heat-sealing and cold sealing. Lidding materials can have a heat-seal coating applied to them; the lidding is then sealed to the backing using heat, which activates the coating. Blister packs can also be sealed using a cold seal process, which uses a combination of a pressure sensitive fold-over blister card and a transparent blister; the blister is trapped between two pieces of board that are bonded together under pressure without using any heat. Additionally, blister packs can be sealed by orienting multiple layers of film properly in order to make a seal.

As used herein, the term "microorganism" refers to a microbe or organism that is unicellular or lives in a colony of cellular organisms. Microorganisms are very diverse; they include, but are not limited to bacteria, fungi, archaea, and protozoans.

Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly breathable, but, at the same time, the material is impermeable to liquid water and microorganisms.

As used herein, the term "sterilization" refers to a means of eliminating or killing microorganisms present on a surface, contained in a fluid or in a compound such as biological culture media in order to achieve asepsis or a sterile microbial environment. Sterilization can be achieved by applying heat, chemicals, irradiation/radiation, high pressure, filtration, or combinations thereof. Chemical sterilization includes sterilization with gases such as ethylene oxide, hydrogen peroxide gas, and ozone, liquids such as chlorine bleach, iodine, glutaraldehyde and formaldehyde, ortho-phthaladehyde (OPA), hydrogen peroxide, peracetic acid, sodium hydroxide, silver, and cobalt. Radiation sterilization involves the use of radiation such as electron beams (E-beam), x-rays, gamma rays, or subatomic particles.

As used herein, the term "knuckle-roll-peel technique" refers to the process whereby a technician, such as a doctor or nurse, opens a package to release the product contained therein. With a knuckle-roll motion, the outer packaging material is peeled apart using two hands, and the inner product is released.

Provided are packages that include a syringe surrounded by a blister package, incorporating elements for opening the blister package with only one hand, while maintaining sterility of the syringe. The package according to one or more embodiments of the present invention uses less material than the conventional two-handed packages. The conventional packages require a peel tab to enable to user/technician to open the package; the peel tab is used by the technician in the knuckle-roll-peel technique. The peel tabs provide a significant amount of additional packaging material, which results in increased waste production for hospitals and other medical settings. For example, on each 10 mL Luer-Lok syringe there is an addition 1 $in^2$ of both top and bottom web material. Thus, by eliminating the peel tab, the package of the present invention can lead to a reduction in as much as 4 billion $in^2$ of world-wide waste. The reduction in waste can translate into cost savings. Additionally, the one-handed packages of the present invention are less cumbersome than the conventional packages, and do not compromise sterility.

Figure 6:
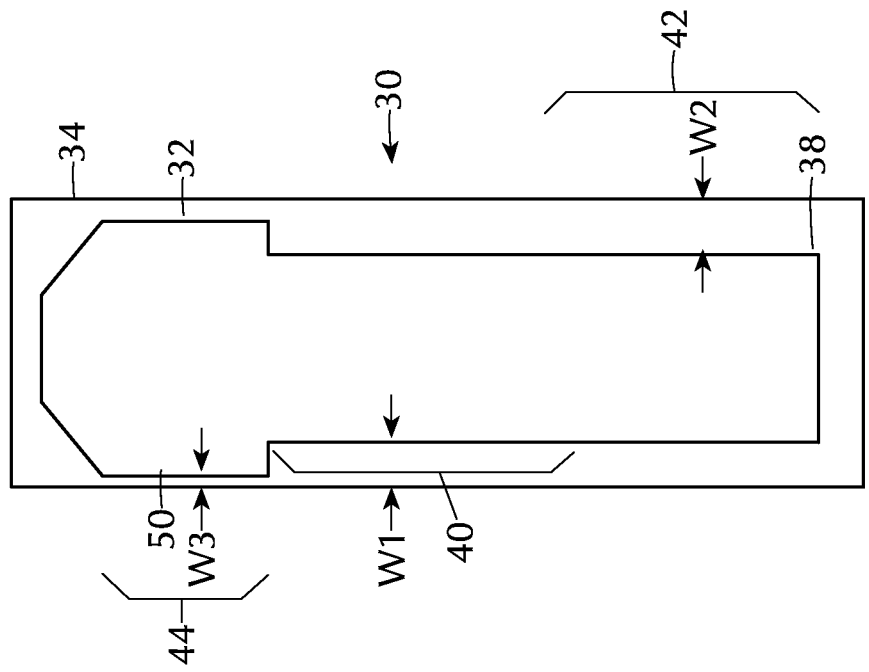
FIG. 6 is a top plan view of a syringe package according to an embodiment of the present invention.
Figure 5:
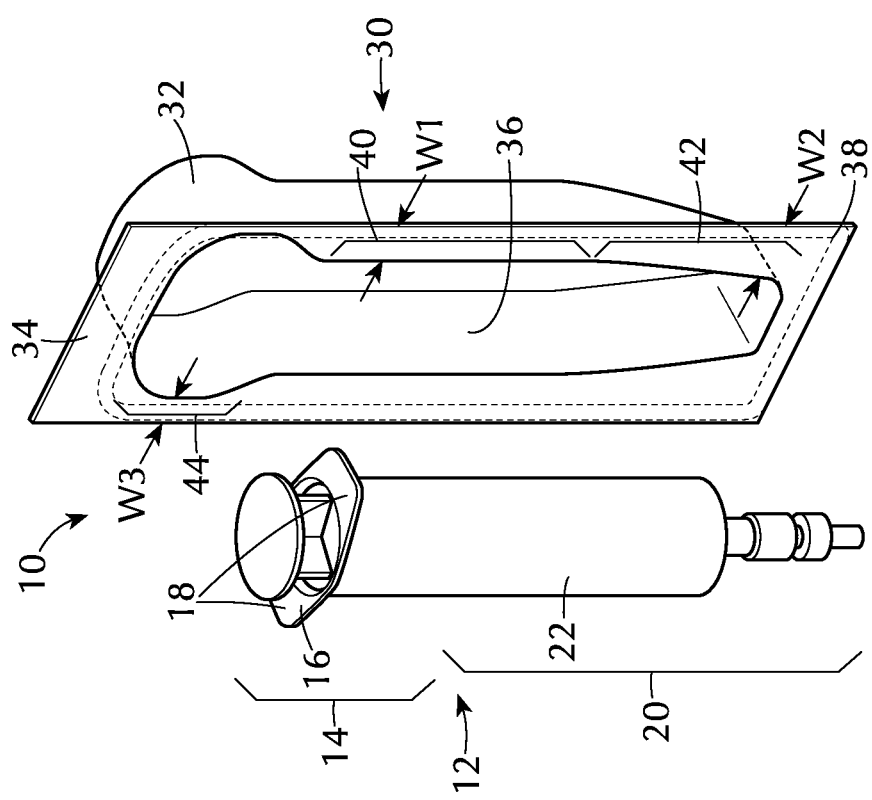
FIG. 5 is a perspective view of a syringe package according to an embodiment of the present invention.

FIGS. 5 and 6 illustrate a syringe package according to one or more embodiments of the present invention. Referring to FIG. 5, the package 10 comprises a syringe 12 comprising a proximal region 14 having a width and including a flange 16 and a flange region 18, a distal region 20 having a width, and a barrel 22 extending from the proximal region 14 to the distal region 20, the flange region 18 having a width that is greater than the width at the distal region 20 and the proximal region 14. The syringe 12 is surrounded by a blister package 30. In one or more embodiments, the syringe 12 is sterile.

Still referring to FIGS. 5 and 6, the blister package 30 comprises a flexible web 32 sealed to a backing 34 defining a compartment 36 for surrounding the syringe 12 and providing a sealed region 38 about a periphery of the backing 34. The sealed region 38 defines a proximal region seal 40 having a width W1, a distal region seal 42 having a width W2, and a flange region seal 44 having a width W3. The flange region seal width W3 is substantially reduced adjacent the flange region 18 compared to the distal region seal width W2 to enable the syringe to be squeezed out of the package with one hand. Upon removal of the syringe 12 from the blister package 30, the flange region 18 and the proximal region 14 of the syringe exit the package 10 prior to the distal region 20.

The flexible web 32 can comprise plastic films such as flexible thermoform able plastics, including, but not limited to, nylon based films with polyethylene and ethyl vinyl acetate (EVA). The backing 34 can comprise Tyvek® or other medical grade materials such as paper or flexible films. The flexible web backing materials are permeable to radiation and to gas, but are not permeable to microorganisms. Thus, the packages according to one or more embodiments can be sterilized.

Referring to FIG. 6, in one or more embodiments, the package 10 can include an escape point 50 along the flange seal region 44. The escape point 50 permits the flange region 18 to exit the package 10 upon squeezing. The holding force at the escape point 50 will vary depending upon the type of syringe 12 contained within the blister package 30. For example, if a ½ mL syringe is contained within the blister package 30 less holding force will be required at the escape point 50 than if a 10 mL syringe is contained within the blister package 30. In other words, the holding force, in one or more embodiments, will be greater for larger syringe products. The escape point 50 is intended to take advantage of the sharpness of the syringe product design, and, therefore, is generally in-line with the flange region 18. The design of the escape point 50 is optimized according to the different medical products (i.e. syringe), particularly with regard to the sizes and shapes of the syringe 12. The escape point 50 has a holding force that is less than the holding force of the rest of the sealed blister package 30. The overall energy required to break the seal of the blister pack is about the same, but the energy required to remove the syringe product 12 through the escape point 50 is significantly less than if the syringe were to exit the blister package 30 at any other point along the seal.

In one or more embodiments, the flange region seal width W3 is reduced by at least $\frac{1}{16}$ adjacent the flange region 18 compared to the distal region seal width W2. In one or more embodiments, the flange region seal width W3 is reduced by at least $\frac{1}{8}$ adjacent the flange region compared to the distal region seal width W2. In one or more embodiments, the flange region seal width is reduced by at least $\frac{1}{4}$ adjacent the flange region compared to the distal region seal width. In one or more embodiments, the flange region seal width W3 is reduced by at least $\frac{1}{2}$ adjacent the flange region compared to the distal region seal width W2.

Figure 7:
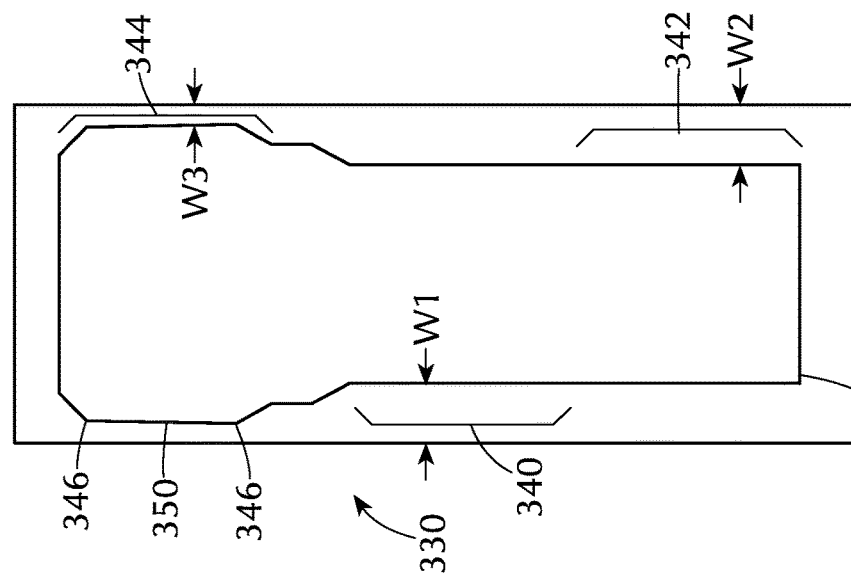
FIG. 7 is a top plan view of a syringe package and a syringe according to an embodiment of the present invention.

Referring to FIG. 7, in one or more embodiments, the sealed region 138 defines a proximal region seal 140 having a width W1, a distal region seal 142 having a width W2, and a flange region seal 144 having a width W3. The flange region seal width W3 is substantially reduced adjacent the flange region compared to the distal region seal width W2 to enable the syringe to be squeezed out of the package with one hand. In one or more embodiments, the flange region seal 144 of the blister package 130 defines a curved radius 146 that provides an escape region 150, having a seal width W3 that is reduced compared to the distal region seal width W2. The escape region 150 permits the syringe to be squeezed out of the package with one hand. The holding force at the escape region 150 will vary depending upon the type of syringe contained within the blister package 130. Larger or heavier syringes are likely to require a higher/larger holding force than smaller or lighter syringes. In one or more embodiments, the flange region seal width W3 is reduced by at least $\frac{1}{16}$ adjacent the flange region compared to the distal region seal width W2. In one or more embodiments, the flange region seal width W3 is reduced by at least $\frac{1}{8}$ adjacent the flange region compared to the distal region seal width W2. In one or more embodiments, the flange region seal width W3 is reduced by at least $\frac{1}{4}$ adjacent the flange region compared to the distal region seal width W2. In one or more embodiments, the flange region seal width W3 is reduced by at least $\frac{1}{2}$ adjacent the flange region compared to the distal region seal width W2. In one or more embodiments, the syringe is sterile.

Figure 8:
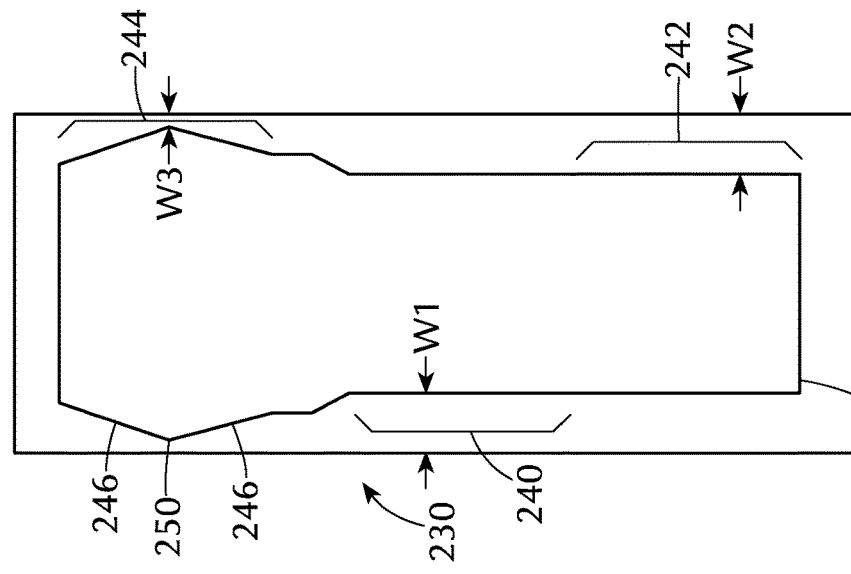
FIG. 8 is a top plan view of a syringe package according to an alternative embodiment of the present invention.

Referring to FIG. 8, in one or more embodiments, the sealed region 238 defines a proximal region seal 240 having a width W1, a distal region seal 242 having a width W2, and a flange region seal 244 having a width W3. The flange region seal width W3 is substantially reduced adjacent the flange region compared to the distal region seal width W2 to enable the syringe to be squeezed out of the package with one hand. In one or more embodiments, the escape point 250 along the flange region seal 244 defines an angled seal region 246 having a seal width W3 that is reduced compared to the distal region seal width W2. The angled seal region 246 can comprise a point of a triangle. The escape point 250 permits the syringe to be squeezed out of the package with one hand. The holding force at the escape point 250 will vary depending upon the type of syringe contained within the blister package 230 and depending upon the materials used to make the blister packaged. In one or more embodiments, the flange region seal width W3 is reduced by at least $\frac{1}{16}$ adjacent the flange region compared to the distal region seal width W2. In one or more embodiments, the flange region seal width W3 is reduced by at least $\frac{1}{8}$ adjacent the flange region compared to the distal region seal width W2. In one or more embodiments, the flange region seal width W3 is reduced by at least $\frac{3}{4}$ adjacent the flange region compared to the distal region seal width W2. In one or more embodiments, the flange region seal width W3 is reduced by at least 50% adjacent the flange region compared to the distal region seal width W2. In one or more embodiments, the syringe is sterile.

Figure 9:
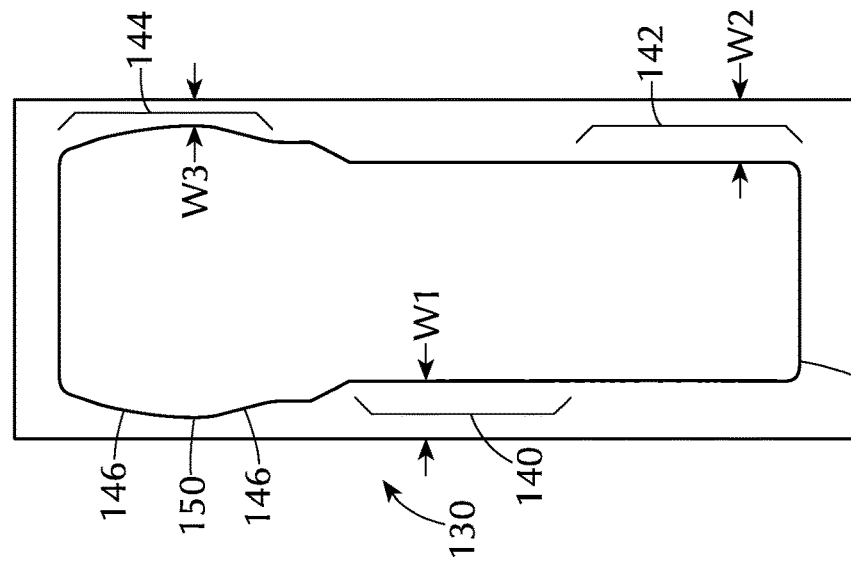
FIG. 9 is a top plan view of a syringe package according to an alternative embodiment of the present invention.

Referring to FIG. 9, in one or more embodiments, the sealed region 338 defines a proximal region seal 340 having a width W1, a distal region seal 342 having a width W2, and a flange region seal 344 having a width W3. The flange region seal width W3 is substantially reduced adjacent the flange region compared to the distal region seal width W2 to enable the syringe to be squeezed out of the package with one hand. In one or more embodiments, the escape point 350 along the flange region seal 344 defines an angled seal region 346 having a seal width W3 that is reduced compared to the distal region seal width W2. The angled seal region 346 can comprise at least two points forming a box. The escape point 350 permits the syringe to be squeezed out of the package with one hand. The holding force at the escape point 350 will vary depending upon the type of syringe contained within the blister package 330. Larger or heavier syringes are likely to require a higher/larger holding force than smaller or lighter syringes. In one or more embodiments, the flange region seal width W3 is reduced by at least $\frac{1}{16}$ adjacent the flange region compared to the distal region seal width W2. In one or more embodiments, the flange region seal width W3 is reduced by at least ⅛ adjacent the flange region compared to the distal region seal width W2. In one or more embodiments, the flange region seal width W3 is reduced by at least ¼ adjacent the flange region compared to the distal region seal width W2. In one or more embodiments, the flange region seal width W3 is reduced by at least ½ adjacent the flange region compared to the distal region seal width W2.

Referring to FIGS. 5 and 6, a second aspect of the present invention is directed to a package 10 comprising a syringe 12 that is typically sterile, the syringe comprising a proximal region 14 having a width and including a flange 16 and a flange region 18, a distal region 20 having a width, and a barrel 22 extending from the proximal region 14 to the distal region 20, the flange region 18 having a width that is greater than the width at the distal region 20 and the proximal region 14. The syringe 12 is surrounded by a blister package 30.

The blister package 30 comprises a flexible web 32 sealed to a backing 34 defining a compartment 36 for surrounding the syringe 12 and providing a sealed region 38 about a periphery of the backing 34. The sealed region 38 having a shape that conforms to the shape of the flange 16 so that the width W3 of the sealed region adjacent to the flange is reduced compared to the width W2 of the sealed region in the distal region. In one or more embodiments, the syringe 12 is sterile. The syringe 12 can be squeezed out of the package 30 with one hand. Upon removal of the syringe 12 from the blister package 30, the flange region 18 and the proximal region 14 exit the package 10 prior to the distal region 20. In one or more embodiments, the flange region seal width W3 is reduced by at least 1/16 adjacent the flange region 18 compared to the distal region seal width W2. In one or more embodiments, the flange region seal width W3 is reduced by at least ⅛ adjacent the flange region compared to the distal region seal width W2. In one or more embodiments, the flange region seal width W3 is reduced by at least ¼ adjacent the flange region compared to the distal region seal width W2. In one or more embodiments, the flange region seal width W3 is reduced by at least ½ adjacent the flange region compared to the distal region seal width W2.

Figure 10:
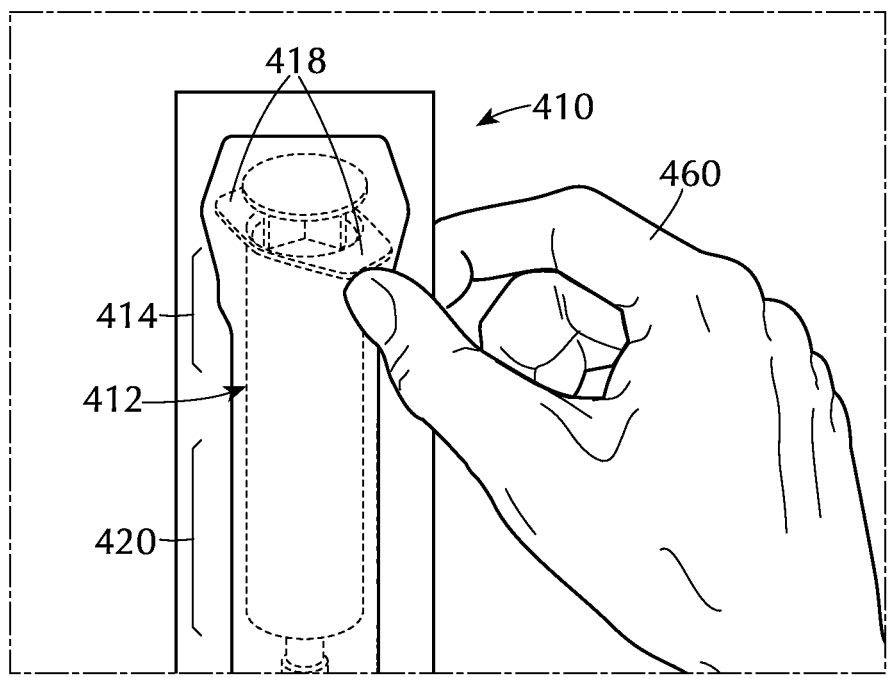
FIG. 10 is a perspective view showing a user/practitioner removing a syringe from a syringe package according to an embodiment of the present invention.
Figure 11:
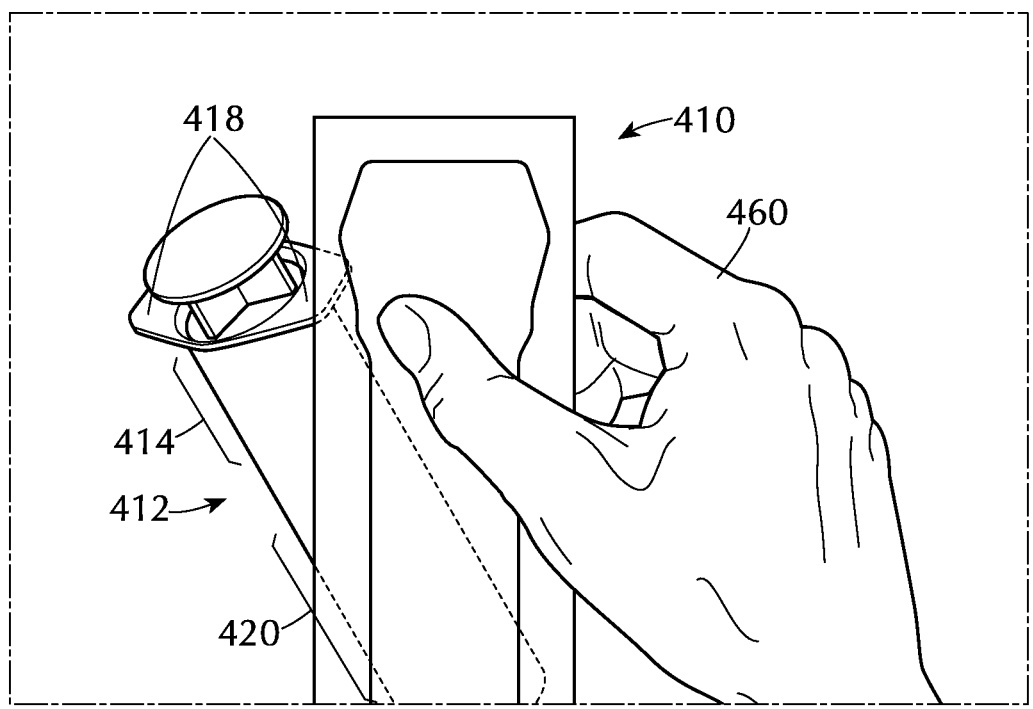
FIG. 11 is a perspective view showing a user/practitioner removing a syringe from a syringe package after squeezing the package shown in FIG. 10.

A further aspect of the present invention is directed to a method of removing a syringe from a package. Referring to FIGS. 10 and 11, the method comprises squeezing the package 410 in the flange region 418. When the package 410 is squeezed, the flange region 418 and the proximal region 414 of the syringe 412 exit the package 410 prior to the distal region 420 of the syringe 412. In one or more embodiments, the syringe 412 is sterile. In one or more embodiments, the package 410 is squeezed in the flange region 418 with only one hand 460. Opening the package with only one hand is less cumbersome for the technician, and enables the technician to use his/her other available hand for additional tasks.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. A method of removing a syringe from a package housing the syringe,
    the package comprising the syringe and a blister package surrounding the syringe;
    the syringe comprising a proximal region having a width including a flange and a flange region, a distal region having a width, and a barrel extending from the proximal region to the distal region, the flange region having a width that is greater than the width at the distal region of the syringe;
    the blister package comprising a flexible web sealed to a backing defining a compartment surrounding the syringe and providing a sealed region about a periphery of the backing, the sealed region defining a proximal region seal having a width, a distal region seal having a width, and a flange region seal having a width, the flange region seal width substantially reduced adjacent the flange region compared to the distal region seal width to enable the syringe to be squeezed out of the package with only one hand without a peel tab;
    the method comprising squeezing the flexible web of the package only at the flange region of the syringe with only one hand such that the flange region of the syringe and the proximal region of the syringe exit the package through the seal adjacent to the flange prior to exit of the distal region of the syringe.

2. The method of claim 1, wherein the sealed region adjacent the flange includes an escape point that permits the flange region to exit the package upon squeezing.

3. The method of claim 2, wherein the escape point defines an angled seal region having a seal width that is reduced compared to the distal region seal width.

4. The method of claim 3, wherein the angled seal region comprises a pointed region.

5. The method of claim 3, wherein the angled seal region comprises at least two points.

6. The method of claim 1, wherein the sealed region adjacent the flange defines a curved radius that provides an escape region and permits the syringe to be squeezed out the package with only one hand.

7. The method of claim 1, wherein the width of the sealed region adjacent the flange is reduced by at least 1/16 compared to the distal region seal width.

8. The method of claim 7, wherein the width of the sealed region adjacent the flange is reduced by at least ⅛ compared to the distal region seal width.

9. The method of claim 8, wherein the width of the sealed region adjacent the flange is reduced by at least ¼ compared to the distal region seal width.

10. The method of claim 9, wherein the width of the sealed region adjacent the flange is reduced by at least ½ compared to the distal region seal width.

11. The method of claim 1, wherein the syringe is sterile.

* * * * *